United States Patent [19]

Anderson

[11] Patent Number: 5,300,065
[45] Date of Patent: Apr. 5, 1994

[54] METHOD AND APPARATUS FOR SIMULTANEOUSLY HOLDING AND SEALING TISSUE

[75] Inventor: Dallas W. Anderson, The Woodlands, Tex.

[73] Assignee: Proclosure Inc., Winter Park, Fla.

[21] Appl. No.: 972,531

[22] Filed: Nov. 6, 1992

[51] Int. Cl.$^5$ .................................... A61N 5/06
[52] U.S. Cl. ............................. 606/13; 606/8; 606/148; 606/16
[58] Field of Search .............. 606/2, 3, 8, 11, 16, 606/151, 148; 128/395, 397

[56] References Cited

U.S. PATENT DOCUMENTS

| | | | |
|---|---|---|---|
| 963,899 | 7/1910 | Kistler | 606/148 X |
| 4,165,747 | 8/1979 | Bermant | 606/148 |
| 4,633,870 | 1/1987 | Sauer | 606/8 |
| 4,655,223 | 4/1987 | Kim | 606/148 |
| 4,672,969 | 6/1987 | Dew | 606/3 |
| 4,854,320 | 8/1989 | Dew et al. | 606/9 X |
| 4,892,098 | 1/1990 | Sauer | 606/8 X |
| 5,002,051 | 3/1991 | Dew et al. | 606/3 X |
| 5,140,984 | 8/1992 | Dew et al. | 606/11 X |
| 5,207,670 | 5/1993 | Sinofsky | 606/8 |

*Primary Examiner*—Peter A. Aschenbrenner
*Attorney, Agent, or Firm*—Steven C. Stewart

[57] ABSTRACT

An apparatus for sealing approximated edges of tissue with thermal energy includes a clamp having members which grasp and hold tissue. A transmissive material is supported by at least one of the members. The members pivot to pull the tissue edges in tight approximation against the transmissive material to form a seam. Thermal energy is then directed at the tissue through the transmissive material and at the seam with sufficient intensity and duration to heat the tissue to an adhesive proteinaceous substance to seal the seam. The approximated seam is held against the transmissive material with an appropriate pressure to avoid over inverted or over everted tissue approximation.

15 Claims, 1 Drawing Sheet

METHOD AND APPARATUS FOR SIMULTANEOUSLY HOLDING AND SEALING TISSUE

BACKGROUND OF THE INVENTION

This invention relates to a method and apparatus for sealing incisions on skin or other organ surfaces by drawing and holding the edges of the incision in tight proximity to form a seam while directing thermal energy onto the seam to denature the protein substance therein.

Optical energy transformed to thermal energy has been used to convert biological tissue into a denatured proteinaceous substance for facilitating healing and wound closure. This healing technique is referred to generally as laser tissue welding. Examples of such laser tissue welding methods are described in U.S. Pat. No.'s 4,672,969, 4,854,320, 5,002,051, and 5,140,984. These methods deliver optical energy to tightly approximated tissue in the vicinity of a wound. This application of thermal energy results in the denaturation of tissue protein including collagen, with disruption of the cell walls which allows the intra- and intercellular fluids to mix. Additional heat further denatures this protein soup which binds together creating something akin to a "biological glue".

In many prior methods of optical energy wound closure, thermal energy is delivered through an optical fiber to the tissue being reconstructed. Typically, one end of the fiber is connected to a laser that supplies optical energy to the wound site. Another end of the fiber is typically spaced a predetermined distance from the tissue, the distance depending on the tissue type. A foot pedal or hand held device activates and deactivates the laser. The parameters such as intensity and duration of the optical energy are controlled so that substantially all of the tissue being heated is raised to a predetermined non-destructive temperature. The minimum predetermined temperature is one at which tissue is converted to a denatured proteinaceous substance. The maximum predetermined temperature is one at which water in the tissue boils.

Critical to tissue welding methods is the necessity to place edges of tissue being repaired in tight approximation. Placing the tissue edges in close or tight proximity allows the denatured tissue constituents to form an intercellular matrix resulting in tissue fusion. Certain skin tissue types require precision when applying the optical energy to seal the edges. A drawback to a current skin tissue welding procedures is that to ensure precision, the optical energy must be applied slowly and carefully thereby increasing the application time.

Another drawback to a laser tissue welding procedure is that when closing an incision, the laser tissue welding surgery can be unnecessarily tedious as the surgeon welds at successive points along the incision. This welding process is complicated because the distal end of the optical fiber that directs the energy for the welding must be placed a predetermined distance to the tissue being reconstructed or the area being reconstructed. If the distal end of the fiber is not at the predetermined distance from the area being sealed or reconstructed, the tissue temperature would be heated outside the aforementioned predetermined temperature range for proper tissue fusion.

SUMMARY OF THE INVENTION

An object of this invention is to provide an improved method and apparatus for reconstructing tissue.

Another object of this invention is to provide an apparatus through which laser welding energy passes and is directed at the tissue that is to be sealed or fused.

It is also an object of this invention to place a device adjacent to the tissue to cause the formation of a proteinaceous framework for denatured protein in the vicinity of biological tissue to seal tissue with greater efficiency and less time.

It is another object of this invention to reconstruct tissue that have incisions or lesions by placing an apparatus above the surface of the tissue and by delivering energy to areas along the incision seam.

It is further an object of this invention to reconstruct tissue with any energy source, such as an ultrasonic or thermal source, while maintaining at all times proper distance between a media delivering the energy to the tissue itself so that the final temperature of the tissue may be precisely maintained.

It is an additional object of this invention to seal an incision in tissue by moving edges of the incision in tight approximation to form a seam and maintaining the edges in alignment while heating the tissue along the seam.

These and other objects are providing with an apparatus for sealing tissue having a first elongated member pivotally engaging a second elongated member to form a clamp that opens and closes. The members have an edge with a surface adapted to grasp tissue and pull the edges of the tissue into close approximation to form a seam when the clamp closes. An energy source provides energy which is capable of heating the tissue to form an adhesive proteinaceous substance. The source is optically coupled to a layer of material that is supported by at least one of the members and that is transmissive to the energy that heats tissue. A delivering device directs energy from the source through the layer of material or through portholes that allow the energy source to be recessed from the tissue at the tissue seam when the edges are pulled into close or tight approximation. The layer of material has a thickness that maintains a predetermined distance between the directing device and the tissue seam when energy from the source is directed at the tissue.

BRIEF DESCRIPTION OF THE DRAWINGS

FIG. 1 is a view of the apparatus holding tissue, and where FIG. 2 is a view of the apparatus prior to grasping the tissue;

DESCRIPTION OF THE PREFERRED EMBODIMENTS

Figure 1:
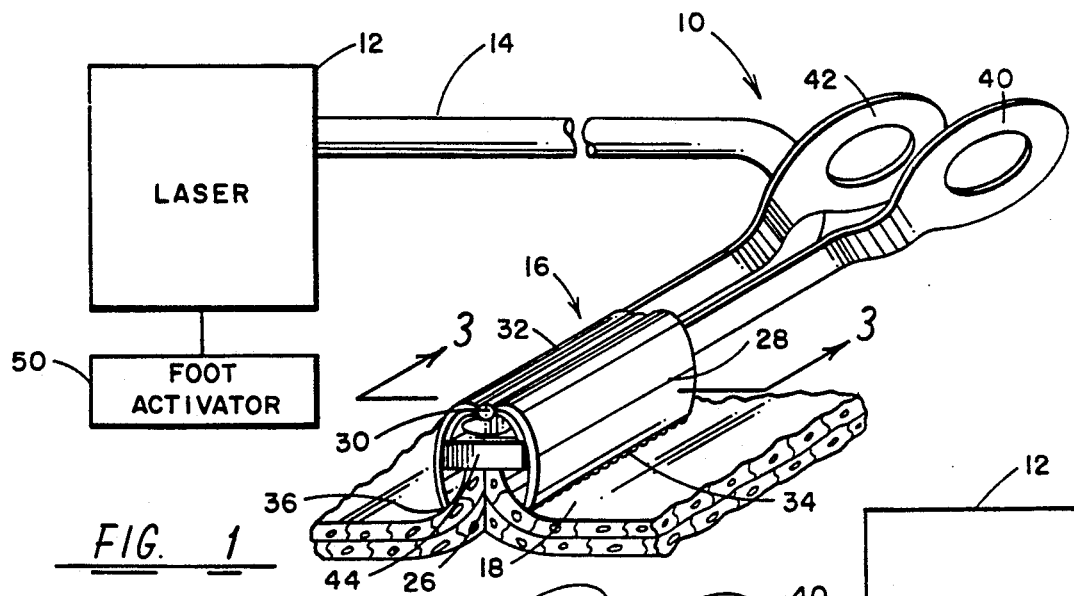
FIGS. 1 and 2 are perspective views of the apparatus for simultaneously sealing and holding tissue, where
Figure 2:
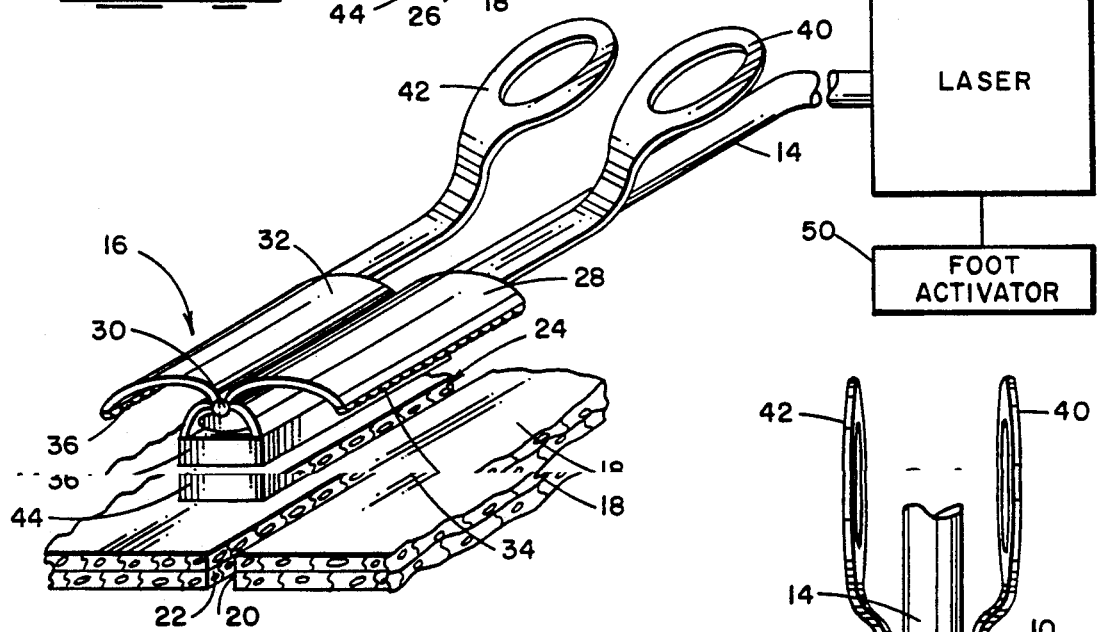
Figure 3:
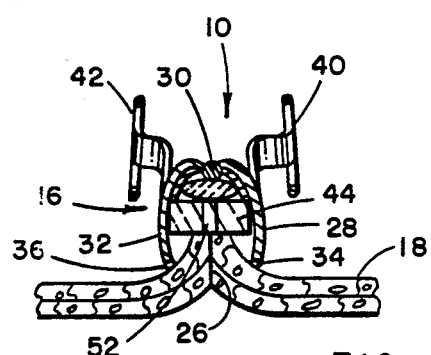
FIG. 3 is a front sectioned view along line 3—3 of FIG. 1.
Figure 4:
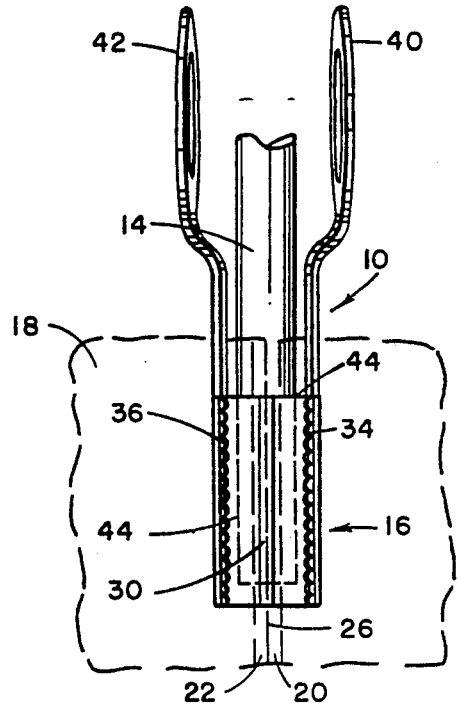
FIG. 4 is a top view of the apparatus shown in FIG. 1.

Referring to FIGS. 1-2, there is shown an apparatus 10 for tissue welding having an energy source 12 optically connected to a proximal end of a delivery device 14. A distal end of delivery device 14 is connected to clamp 16. Clamp 16 engages with tissue 18 to pull edges 20 and 22 of lesion or incision 24 together in tight contact to form a seam 26. Once engaged, optical energy from source 12 is fed through device 14 and clamp 16 to seam 26. The optical energy is applied with sufficient amplitude and duration to heat tissue 18 to an adhesive proteinaceous substance to seal the seam 26.

Referring to FIGS. 1-4, clamp 16 includes a first elongated member 28 pivotally connected with rod 30 to second elongated member 32. A spring (not shown) may be attached to rod 30 and members 28 and 32 to close clamp. First and second elongated members 28 and 32 have edges 34 and 36 respectively which engage the surface of tissue 18. Edges 34 and 36 extend parallel to each other and seam 26. Connected to one end of members 28 and 32 are handles 40 and 42 which permit a user to rotate members 28 and 32 on rod 30.

Connected to and extending parallel to rod 30 between members 28 and 32 is transmissive material 44. Material 44 is transparent to energy being emitted through delivery device 14 to seal seam 26. Material 44 has two functions. First when edges 20 and 22 are pulled in tight contact, the tissue 18 contacts material 44 and its edges are held in alignment. Thus material 44 prevents tissue edges 20 and 22 from becoming overly everted or inverted. Second, Material 44 maintains the proper spacing between the distal end of device 14 and the surface of tissue 18. By maintaining the proper spacing, the tissue 18 is precisely heated to a predetermined temperature range bounded by a minimum temperature at which tissue denatures, and a maximum temperature at which water in tissue boils.

The preferred thickness of the transmissive material when the tissue 18 is skin is summarized in the following Table I. These parameters are by no means all exclusive; it is envisioned that other parameters can be used with modifications and it is intended that this table be exemplary of a preferred embodiment only.

TABLE I

| LASER PARAMETERS FOR SKIN TISSUE | | | | | |
|---|---|---|---|---|---|
| Tissue Thickness (mm) | Material Thickness (mm) | Spot Size Diameter (with 400 μfiber) | Range of Power (Watts) | Exposure Duration On/Off | Approx. Tissue Final Energy Transferred J/CM² |
| 3 | 3 | .925–1.14 mm | 1.65–1.85 | 1.0 sec/1.0 sec | 13.31 |

Rather than directing energy through material 44, delivery device 14 may optionally direct energy through a porthole 52 (FIG. 3) in material 44 that allows the distal end of device 14 to be recessed from tissue 18. In another embodiment, delivery device 14 be positioned in material 44 to directly contact tissue 18.

Energy source 12 is preferably a Laser energy source emitting coherent light energy from about 1.2 to 1.4 micrometers. Energy source 12 is preferably enabled and disabled by a foot activator 50 or a switch (not shown) positioned on handle 40 or 42.

The distal end of delivery device 14 is positioned between material 44 and rod 30. The delivery device 14 which source 12 is connected, is preferably a fiber optic cable which is capable of side firing at its distal end (See FIG. 4). Although a side firing optic cable is shown as delivery device 14, cables which have end firing may be used as well.

During operation of apparatus 10, clamp 16 is positioned over incision 24 so that delivery device 14 distal end aligns with the incision 24. Once in position, handles 40 and 42 are rotated by the user so that edges of members 28 and 32 engage the surface of tissue 18. Handles 40 and 42 continue to be rotated to draw tissue edges 20 and 22 in tight proximity and in contact with material 44.

Once tissue edges 20 and 22 are in tight proximity and in contact with material 44, foot activator 50 is depressed to enable source 12. Thermal energy from source 12 is delivered through device 14, material 44 to seam 26 of tissue 18. Device 14 preferably delivers energy through material 44 and along the entire length of seam 26.

Alternately device 14 delivers thermal energy to a portion of seam 25 and then clamp 16 is opened, moved to a new location over seam 26. Once positioned over the new location, the clamp 16 would be closed to tightly approximate the edges 20 and 22 of the tissue 18 at the new location, and then thermal energy would be delivered to the new seam 26 location to seal the incision 24.

The thermal energy from source is delivered with sufficient amplitude and duration to heat tissue 18 to a predetermined non-destructive temperature range. This range is bounded by a minimum rate at which tissue forms a denatured proteinaceous substance and a maximum rate at which water in tissue boils. The preferred maximum temperature at which the tissue 18 is heated is slightly less than the temperature tissue shrinkage occurs.

Once the tissue 18 has been heated to the predetermined non-destructive temperature range, the foot activator 50 would be depressed to disable energy source 12. Handles 40 and 42 would then pivot members 28 and 32 to open clamp 16 and release tissue 18.

This concludes the description of the preferred embodiments. A reading by those skilled in the art will bring to mind various changes without departing from the spirit and scope of the invention. It is intended, however, that the invention only be limited by the following appended claims.

I claim:

1. An apparatus for sealing approximated edges of tissue comprising:
   a first elongated member pivotally engaging a second elongated member to form a clamp that opens and closes, said members having an edge with a surface adapted to grasp tissue and pull the edges of the tissue into tight approximation to form a seam when said clamp closes;
   an energy source for providing energy which is capable of heating the tissue to form an adhesive proteinaceous substance; and
   a layer of material supported by at least one of said members and transmissive to energy that heats tissue.
   means for directing energy from said source through said layer of material at said tissue seam when said edges are pulled into tight approximation; and
   said layer of material having a thickness that maintains a predetermined distance between said directing means and said tissue seam when energy from said source is directed at the tissue.

2. The apparatus as recited in claim 1 wherein said directing means includes a fiber optic cable that is connected at one end to the source and abuts said layer of material at its other end.

3. The apparatus as recited in claim 2 wherein said end of the optic cable that abut said material is positioned to direct energy along said seam.

4. The apparatus as recited in claim 1 further comprising means for enabling and disabling said energy source.

5. The apparatus as recited in claim 1 wherein said material is placed between said clamps so that when said clamps pull said tissue together said seam of said tissue contacts said material.

6. The apparatus as recited in claim 1 wherein the edges of the members extend in parallel along the surface of the tissue.

7. A method for sealing approximated edges of a tissue wound, the method comprising the steps of:
 pivotally engaging a first elongated member with a second elongated member to form a clamp that opens and closes;
 forming tissue engaging edges with said members;
 extend in said engaging edges substantially parallel to each other;
 positioning both parallel extending edges in a plane parallel to the plane of the surface of the tissue;
 grasping tissue with the edges of said members;
 closing the clamp when grasping the tissue to pull the edges of the tissue wound into tight approximation;
 forming a seam along the tightly approximated edges of the tissue wound when said clamp grasping the tissue closes;
 providing energy from a source which is capable of heating the tissue to form an adhesive proteinaceous substance; and
 directing energy with a delivery means from said source at said tissue seam when said edges are pulled into tight approximation to seal the seam.

8. A method for sealing approximated edges of tissue, the method comprising the steps of:
 pivotally engaging a first elongated member with a second elongated member to form a clamp that opens and closes;
 grasping tissue with an edge of at least one of said members;
 closing the clamp when grasping the tissue to pull the edges of the tissue into tight approximation;
 forming a seam along the tightly approximated edges of the tissue when said clamp grasping the tissue closes;
 providing energy from a source which is capable of heating the tissue to form an adhesive proteinaceous substance;
 directing energy with a delivery means from said source at said tissue seam when said edges are pulled into tight approximation to seal the seam;
 positioning a layer of material that is transmissive to energy from the source between the delivery means and the seam; and
 selecting the thickness of the material to maintain a predetermined distance between said delivering means and said tissue seam when energy from said source is directed at the tissue.

9. The method as recited in claim 7 further comprising the step of controlling the energy directed at the seam to heat the tissue to a temperature within a nondestructive range bounded by a minimum temperature at which tissue forms a denatured proteinaceous substance and a maximum temperature at which water in the tissue would boil.

10. The method as recited in claim 9 further comprising the step of opening the clamp and releasing the tissue after energy has been directed at the seam to heat the tissue to the nondestructive range.

11. The method as recited in claim 8 further comprising the steps of holding the tissue with the clamp with sufficient pressure to force the seam to contact the material; and maintaining the contact between the seam and the material while the energy is being directed at the seam to heat the tissue to the nondestructive range.

12. The method as recited in claim 11 further comprising the step of applying pressure to the tissue with the clamp to force the seam to contact the material while preventing the edges of the tissue from becoming everted or inverted.

13. The method as recited in claim 9 further comprising the step of extending the edges of the members along a surface of the tissue substantially parallel to the seam when grasping the tissue.

14. A method for sealing approximated edges of tissue, the method comprising the steps of:
 pivotally engaging a first elongated member with a second elongated member to form a clamp that opens and closes;
 grasping tissue with an edge of at least one of said members;
 closing the clamp when grasping the tissue to pull the edges of the tissue into tight approximation;
 forming a seam along the tightly approximated edges of the tissue when said clamp grasping the tissue closes;
 providing energy from a source which is capable of heating the tissue to form an adhesive proteinaceous substance;
 directing energy with a delivery means from said source at said tissue seam when said edges are pulled into tight approximation to seal the seam; and
 contacting the seam with a material that prevents the edges of the tissue from becoming everted and inverted when the tissue edges are pulled into tight approximation.

15. The method as recited in claim 14 further comprising the steps of:
 placing a porthole in the material; and
 directing energy from the delivery means of the seam through the porthole.

* * * * *